US012627311B2

(12) United States Patent
Tailliet et al.

(10) Patent No.: US 12,627,311 B2
(45) Date of Patent: May 12, 2026

(54) ANALOG-DIGITAL CONVERTER AND METHOD

(71) Applicant: STMicroelectronics International N.V., Geneva (CH)

(72) Inventors: François Tailliet, Fuveau (FR); Marc Battista, Allauch (FR)

(73) Assignee: STMicroelectronics International N.V., Geneva (CH)

( * ) Notice: Subject to any disclaimer, the term of this patent is extended or adjusted under 35 U.S.C. 154(b) by 124 days.

(21) Appl. No.: 18/585,766

(22) Filed: Feb. 23, 2024

(65) Prior Publication Data

US 2024/0333293 A1 Oct. 3, 2024

(30) Foreign Application Priority Data

Mar. 30, 2023 (FR) ...................................... 2303071

(51) Int. Cl.
| | |
|---|---|
| *H03M 1/12* | (2006.01) |
| *A61B 5/021* | (2006.01) |
| *G01R 19/252* | (2006.01) |
| *G01R 23/10* | (2006.01) |

(52) U.S. Cl.
CPC ........... *H03M 1/12* (2013.01); *A61B 5/02108* (2013.01); *G01R 19/252* (2013.01); *G01R 23/10* (2013.01)

(58) Field of Classification Search
CPC .... H03M 1/12; A61B 5/02108; G01R 19/252; G01R 23/10
See application file for complete search history.

(56) References Cited

U.S. PATENT DOCUMENTS

| | | | | |
|---|---|---|---|---|
| 5,902,933 A | * | 5/1999 | Bingo | ................... G01L 9/0072 |
| | | | | 361/283.4 |
| 6,111,533 A | | 8/2000 | Yuan et al. | |
| 2012/0039588 A1 | | 2/2012 | Harada et al. | |

* cited by examiner

*Primary Examiner* — Joseph J Lauture
(74) *Attorney, Agent, or Firm* — Slater Matsil, LLP

(57) ABSTRACT

A method for controlling an analog-digital converter comprising first and second oscillators, and first and second elements, the method comprising a first step during which the first and second oscillators generate frequencies depending on an electrical characteristic of the first element and of the second element, respectively, and a second step during which the first and second oscillators generate frequencies depending on the electrical characteristic of the second element and of the first element, respectively.

20 Claims, 3 Drawing Sheets

ANALOG-DIGITAL CONVERTER AND METHOD

CROSS-REFERENCE TO RELATED APPLICATIONS

This application claims the priority benefit of French patent application number FR2303071, filed on Mar. 30, 2023, entitled "Convertisseur analogique-numérique," which is hereby incorporated herein by reference to the maximum extent allowable by law.

TECHNICAL FIELD

The present description relates generally to electronic devices and methods, and more particularly to analog-digital converters and methods. The embodiments described relate more particularly to methods and converters based on oscillators.

BACKGROUND

An analog-digital converter is an electronic device the function of which is to translate an analog quantity into a digital value encoded on a plurality of bits. The converted signal is generally an electrical voltage.

Some converters use variations of a frequency of an oscillator, which are generated by variations of a physical characteristic (or quantity) measured by a sensor, e.g., temperature, pressure, relative humidity, light, etc. The electrical properties of the sensor vary the frequency, and a measurement of an information representative of the frequency provides a conversion into a digital value representative of the physical quantity measured.

However, such converters are sensitive to variations of an operating characteristic of the circuit, e.g., the supply voltage, to the aging thereof, or to variations in the manufacturing process.

SUMMARY

One embodiment addresses all or some of the drawbacks of known analog-digital converters.

One embodiment provides a method for controlling an analog-digital converter comprising first and second oscillators, and first and second elements, the method comprises a first step during which the first and second oscillators generate frequencies depending on an electrical characteristic of the first element and of the second element, respectively, and a second step during which the first and second oscillators generate frequencies depending on the electrical characteristic of the second element and of the first element, respectively.

Another embodiment provides an analog-digital converter comprising first and second oscillators, and first and second elements, wherein the first and second oscillators are configured for generating, during a first step, frequencies depending on an electrical characteristic of the first element and of the second element, respectively, and during a second step, frequencies depending on the electrical characteristic of the second element and of the first element, respectively.

According to one embodiment, the first and second oscillators are identical.

According to one embodiment, the electrical characteristic of the first element is sensitive to variations of a physical quantity, the electrical characteristic of the second element being insensitive to variations of the physical quantity.

According to one embodiment, the first element is a sensor.

According to one embodiment, the converter comprises first and second counters configured so that during the first step, the first counter counts the oscillations of the first oscillator and the second counter counts the oscillations of the second oscillator; and during the second step, the first counter counts the oscillations of the second oscillator and the second counter counts the oscillations of the first oscillator.

According to one embodiment, the second counter triggers, when same reaches a reference value, the stopping of the oscillator associated with the first counter.

According to one embodiment, the first and second counters provide values representative of the values of the respective electrical characteristics of the first and second elements.

According to one embodiment, the first counter supplies a value representative of a current value of the physical quantity.

In one embodiment, the converter includes a circuit configured for generating an oscillator control signal associated with the first element according to the state of an enabling signal of the oscillator associated with the second element and to the value of the second counter.

BRIEF DESCRIPTION OF THE DRAWINGS

The foregoing features and advantages, as well as others, will be described in detail in the following description of specific embodiments given by way of illustration and not limitation with reference to the accompanying drawings, wherein.

DETAILED DESCRIPTION OF ILLUSTRATIVE EMBODIMENTS

Like features have been designated by like references in the various figures. In particular, the structural and/or functional features that are common among the various embodiments may have the same references and may dispose identical structural, dimensional and material properties.

For the sake of clarity, only the operations and elements that are useful for an understanding of the embodiments described herein have been illustrated and described in detail.

Unless indicated otherwise, when reference is made to two elements connected together, this signifies a direct connection without any intermediate elements other than conductors, and when reference is made to two elements coupled together, this signifies that these two elements can be connected or they can be coupled via one or more other elements.

In the following disclosure, unless indicated otherwise, when reference is made to absolute position qualifiers, such as the terms "front," "back," "top," "bottom," "left," "right," etc., or to relative positional qualifiers, such as the terms "above," "below," "higher," "lower," etc., or to qualifiers of orientation, such as "horizontal," "vertical," etc., reference is made to the orientation shown in the figures, unless otherwise specified.

Unless specified otherwise, the expressions "around," "approximately," "substantially" and "in the order of" signify within 10%, and preferably within 5%.

The described embodiments provide for the use of a converter equipped with two oscillators, the respective oscillation frequencies of which are sensitive to the variations of an electrical characteristic of two different elements or sensors, the characteristic being sensitive to the variations of a physical quantity. The two elements or sensors are chosen so that the respective electrical characteristics thereof have variations that are different, e.g., inverse, from the variations of the physical quantity.

The use of an architecture comprising two oscillators, configured for comprising two measurement phases with a permutation between the two phases, counters and elements determining the variations of frequency, compensates for the measurement errors due to the aging of the oscillators or the dependence thereof on the supply voltage.

Figure 1:
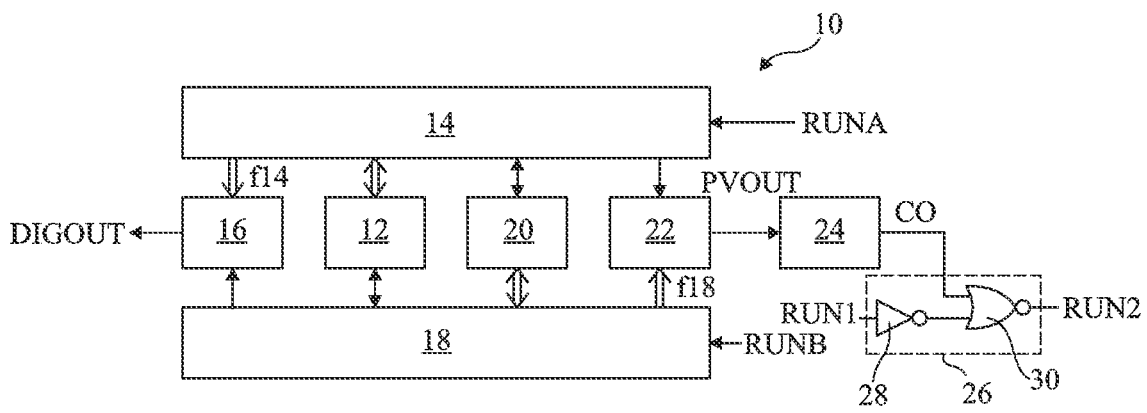
FIG. 1 schematically illustrates an embodiment of an analog-digital converter.

FIG. 1 schematically illustrates an embodiment of an analog-digital converter 10.

The converter 10 is configured for converting analog information coming from, inter alia, an element 12, into digital values. The analog information comes e.g., from an element 20. The element 12 is e.g., a sensor, e.g., a temperature sensor, a pressure sensor, a relative humidity sensor, a light sensor, etc.

The converter 10 comprises an oscillator 14. The oscillator 14 is configured for generating a periodic voltage having a frequency f14. In other words, the oscillator is configured for generating a frequency f14. The oscillator 14 comprises an input configured for receiving an enabling signal, e.g., a signal RUNA. For example, the signal RUNA is a binary signal taking a first value for setting the oscillator in an active mode wherein an output frequency, e.g., the frequency f14, is provided and a second value for setting the oscillator in an inactive or sleep mode wherein the output frequency is not provided.

In the active mode, the converter 10 comprises a first operating mode, illustrated by double arrows, wherein the oscillator 14 is configured in such a way that the operating frequency f14 is dependent on an electrical characteristic of the element 12. The electrical characteristic is e.g., the resistivity of the element 12, which is sensitive to the variations of the physical characteristic measured, e.g., the temperature. The above is an example and, depending on the nature of the sensor, the electrical characteristic that makes the frequency f14 vary can be other than the resistivity (e.g., the inductance, the capacitance or the impedance). Preferentially, the frequency f14 is a monotonic function of the characteristic of the element 12. For example, the electrical characteristic can be an impedance (capacitance, inductance), or an electrical quantity (voltage, current) representative of the physical quantity to be measured. The electrical characteristic controls the frequency of the oscillator connected to the element 12. Thereby, a voltage or a current can be generated by devices such as devices for generating proportional to absolute temperature (PTAT) voltages or complementary to absolute temperature (CTAT) voltages.

In the first operating mode, the frequency f14 is supplied to a counter 16. The counter 16 is configured for counting the oscillations of the frequency f14. The counter 16 generates a value DIGOUT corresponding to the number of oscillations counted by the counter 16. The digital value DIGOUT is representative of the value of the physical quantity measured by the sensor 12.

The converter 10 comprises a second oscillator 18. The oscillator 18 is e.g., identical to the oscillator 14. The oscillators 14 and 18 are e.g., supplied by the same supply voltage.

The oscillator 18 is configured for generating a periodic voltage having an operating frequency f18. The oscillator 18 comprises an input configured for receiving an enabling signal, e.g., a signal RUNB. For example, the signal RUNB is a binary signal taking a first value for setting the oscillator in an active mode wherein an output frequency, frequency f18, is provided and a second value for setting the oscillator in an inactive or sleep mode wherein the output frequency is not provided.

In the first operating mode of the converter 10, the oscillator 18 is configured in such a way that the operating frequency f18 is dependent on an electrical characteristic of the element 20. Element 20 is different (distinct) from element 12, i.e., it is a different component. The electrical characteristic is e.g., like for the element 12, the resistivity of the element 20. The characteristic can be a characteristic different from the characteristic of the element 12. According to a particular embodiment, the element 20 serves as a reference element and the variations of frequency generated by the variations of the physical quantities of the elements 12 and 20 are thus really different. For example, element 20 is insensitive to the variations of the physical quantity measured by the element 12, e.g., the temperature. According to another example, the element 20 is inversely sensitive to the variations of the physical quantity measured by the element 12. Insensitive refers to an element 20 the sensitivity of which to the physical quantity, is at least 2 times, preferentially at least 5 times smaller than same of the element 12. Inversely sensitive means that when the characteristic of the element 12 is increasing, decreasing respectively, the characteristic of the element 20 is decreasing, increasing respectively. Preferentially, the frequency f18 is a monotonic function of the characteristic of the element 20.

In the first operating mode, the frequency f18 is supplied to a counter 22. The counter 22 is configured for counting the oscillations of the frequency f18. The counter 22 generates a value PVOUT corresponding to the number of oscillations counted by the counter 22. The digital value PVOUT is representative of the value of the physical quantity measured by the sensor 20.

The converter 10 further comprises a comparator 24. The comparator 24 is configured for comparing the value PVOUT with a reference value PV. The value PV is e.g., programmed in the comparator 24 or contained in a non-volatile storage register and supplied to the comparator 24 when the converter is enabled, e.g., by a state machine that controls the device 10. The comparator 24 is configured for generating a binary signal CO representing the result of the comparison between the value PVOUT and the reference value PV. For example, the signal CO has a first value, e.g., the binary value '1', when the value PVOUT is greater than or equal to the reference value and has a second value, e.g., the binary value 'o', when the value PVOUT is less than the reference value. The signal PVOUT, through the comparison between the count of the number of oscillations generated by element 20 with the reference value, indicates the moment when the value supplied by the counter DIGOUT can be output from the circuit as being representative of the current value of the physical quantity measured by the element 12, and the physical quantity measured by the element 20.

Preferentially, the converter further comprises a circuit 26 configured for generating the enabling signal of the oscillator (14 in the first operating mode) associated with the element (12) and the counter (16) on the basis of the enabling signal of the other oscillator (associated with the reference element 20) and of the signal CO, in order to stop the oscillator associated with the element 12 and thereby make the output of the counter 16, and thus the value DIGOUT, stable.

The circuit 26 receives as inputs a binary signal RUN1 (equal to the signal RUNB in the first operating mode described hereinabove), corresponding to the enabling signal of the oscillator associated with the element 20, and the value CO, and supplies a binary signal RUN2 (equal to the signal RUNA in the first operating mode) for enabling the oscillator associated with the element 12. The circuit 26 is configured so that:

when the signal RUN1 has a value (e.g., 0) indicating a stop or sleeping of the oscillator associated with the element 20, the signal RUN2 has the same value indicating a disabled state of the oscillator associated with element 12 (both oscillators being stopped, the outputs DIGOUT and PVOUT of both counters 16 and 22 are zero);

when the signal RUN1 has a value (e.g., 1) indicating the enabling of the oscillator associated with the element 20 and the signal CO has the second value (PVOUT<PV), the signal RUN2 has the same value 1 indicating the enabling of the oscillator associated with the element 12; and when the signal RUN1 has the value (e.g., 1) indicating the enabling of the oscillator associated with the element 20 and the signal CO has the first value (PVOUT>=PV), the signal RUN2 takes the value indicating the stop or sleeping of the oscillator associated with the element 12.

In the example shown in FIG. 1, the circuit 26 comprises an inverter circuit 28 and a NOR logic gate 30. The inverter circuit 28 comprises an input configured for receiving the signal RUN1, and an output on which is generated a signal complementary to the signal RUN1. The logic gate 30 comprises an input on which the signal CO is received and another input linked, preferentially connected, to the output of the inverter circuit 28. The logic gate 30 further comprises an output at which the signal RUN2 is generated. The value DIGOUT supplied by the counter 16 is proportional to the value PV and to the ratio of the frequencies between the oscillators 14 and 18. Such frequencies are controlled by the impedances 12 and 20, respectively. Even if the two oscillators are identical, the impedance-frequency relationship (or more generally the value derived from the sensor-frequency) of the two oscillators can differ slightly depending upon the supply voltage, the aging, and the variations of the manufacturing process. The above affects the value DIGOUT and makes same potentially dependent on the variations of the supply voltage, on aging, and on the variations of the manufacturing process.

According to the embodiments described, it is provided for attenuating the impact of the variations of the supply voltage, to aging, and of the variations of the manufacturing process, by successively using the two oscillators 14 and 18 for measuring the physical quantity of the element 12. For this purpose, two phases, cycles or steps, of operation are provided for, wherein, during a first phase, the device is configured for operating according to the first mode described hereinabove and, during a second phase, the device is configured so that, according to a second operating mode, the oscillator 14 is associated with the element 20 and the oscillator 18 is associated with the element 12.

Thereby, in the second operating mode of the converter 10, illustrated by single arrows, the oscillator 14 is configured in such a way that the operating frequency f14 is dependent on the electrical characteristic of the element 20 and the oscillator 18 is configured in such a way that the operating frequency f18 is dependent on the electrical characteristic of the element 12. In other words, the inputs/outputs of the oscillators 14 and 18 are interchanged. In the second operating mode, the frequency f14 is thus supplied to the counter 22. The value PVOUT then corresponds to the number of oscillations counted by the counter 22. The frequency f18 is supplied to the counter 16. The value DIGOUT then depends on the number of oscillations counted by the counter 16. In order to take into account, the two operating modes in the final value, the counter 16 is not reset between the two phases and thus cumulates the contributions of the two oscillators. It is enough to take same into account in the understanding of the conversion result, e.g., by dividing the value DIGOUT by two.

In the second operating mode of the converter 10, illustrated by single arrows, the oscillator 14 is configured in such a way that the frequency is dependent on the electrical characteristic of the element 20 and the oscillator 18 is configured in such a way that the frequency f18 is dependent on the electrical characteristic of the element 12. In the second operating mode, the frequency f14 is supplied to the counter 22 and the value DIGOUT then corresponds to the number of oscillations counted by the counter 22. The frequency f18 is supplied to the counter 16 and the value DIGOUT corresponds to the number of oscillations counted by the counter 16. Furthermore, the respective signals RUNA and RUNB for controlling the oscillators 14 and 18 are also inverted, the signal RUNA for enabling the oscillator 14 corresponding to the signal RUN1 and the signal RUNB for enabling the oscillator 18 corresponding to the signal RUN2.

Figure 2A:
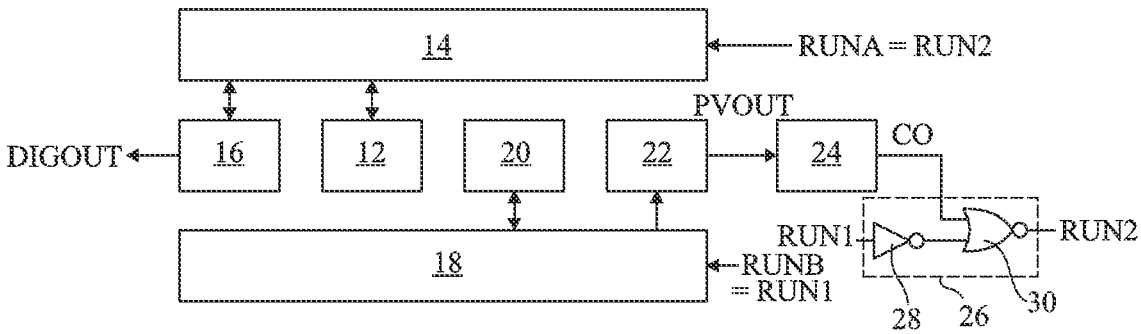
FIG. 2A schematically illustrates a step of an embodiment of the analog-digital converter shown in FIG. 1.
Figure 2B:
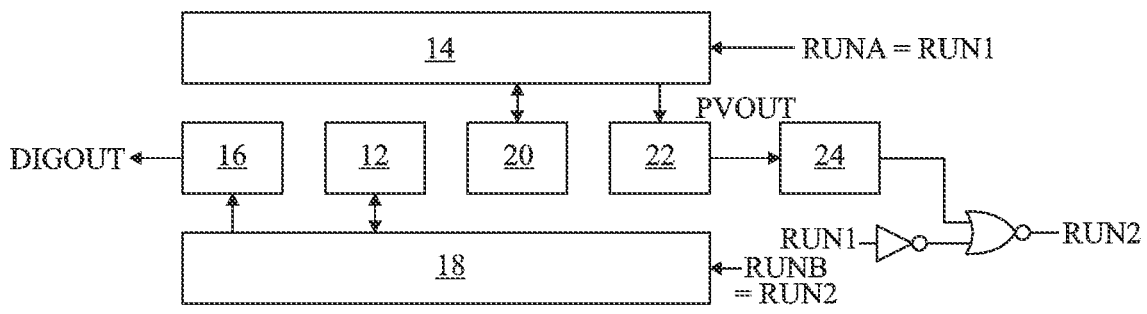
FIG. 2B schematically illustrates another step of an embodiment of the analog-digital converter of FIG. 1.

In order to be able to supply the oscillators 14 and 18 with the appropriate signals RUN1 and RUN2, the converter comprises, e.g., one or a plurality of multiplexers (not shown) controlled by a signal indicative of the active phase or operating mode. The signal indicative of the operating phase serves e.g., to control switches between the circuits 12, 16, 20 and 22 and the oscillators 14 and 18, so as to associate appropriate elements and counters with the oscillators 14 and 18. FIGS. 2A and 2B illustrate an embodiment of the converter shown in FIG. 1, i.e., illustrate an analog-digital conversion method. The embodiment comprises a first step during which the converter is in the first operating mode, illustrated by FIG. 2A, and a second step during which the converter is in the second operating mode, illustrated by FIG. 2B. Preferentially, each first step is followed, preferentially directly followed, by a second step. The order of the steps illustrated in FIGS. 2A and 2B can be reversed.

FIG. 2A schematically illustrates a step of an embodiment of the analog-digital converter shown in FIG. 1. More precisely, FIG. 2A illustrates a first step during which the converter is in the first operating mode.

Before starting the first step, the counters 16 and 22 are reset. Thereby, the values of the signals DIGOUT and PVOUT are equal to a reset value, e.g., a zero value.

In the first operating mode, the enabling signal received by the oscillator 14 is the enabling signal RUN2 and the enabling signal received by the oscillator 18 is the signal RUN1.

During the start of the first step, the signal RUN1 takes the value indicating the enabling of the oscillator 18. The counter 22 having been reset, the value PVOUT is less than the comparison (or reference) value PV. Therefore, the signal RUN2 generated at the output of the circuit 26 has the value indicating the enabling of the oscillator 14.

The oscillators 14 and 18 generate voltages having the frequencies f14 and f18, respectively. The values DIGOUT and PVOUT increase, the counters 16 and 22 counting the oscillations of the voltages generated by the oscillators 14 and 18. When the value PVOUT reaches the reference value PV, the signal RUN2 takes the value that stops the oscillator 14. In other words, the signal RUNA takes the value that stops the oscillator 14.

The oscillation time D1, i.e., the time between the enabling of the oscillator 18 and the stopping of the oscillator 14, obeys the following equation:

$$D1 = DIGOUT1 * t14(D12)$$
$$= PV * t18(D20),$$

wherein DIGOUT1 is the value taken by the counter 16 at the end of the time D1, PV is the value of the signal PVOUT after the time D1, i.e., the reference value, t14 (D12) corresponds to the period of the oscillator 14 associated with the element 12 and t18 (D20) corresponds to the period of the oscillator 18 associated with the element 20.

In other words, the value DIGOUT1 satisfies the following equation:

$$DIGOUT1 = PV * t18(D20)/t14(D12)$$
$$= PV * f14(D12)/f18(D20),$$

wherein f14 (D12) corresponds to the frequency of the oscillator 14 associated with the element 12 and f18 (D20) corresponds to the frequency of the oscillator 18 associated with the element 20.

The periods of the oscillators 14 and 18 can be expressed by the following equations:

$$t14(D12) = K14 * Z12 + L14; \text{ and}$$
$$t18(D20) = K18 * Z20 + L18,$$

wherein the values Z12 and Z20 correspond respectively to the impedances of the elements 12 and 20, the values K14 and K18 corresponding to the coefficients of proportionality between the impedance Z12 or Z20 of the element 12 and 20 with which the oscillator 14 and 18 are respectively associated and the respective periods thereof, and the values L14 and L18 correspond respectively to the delays generated by the internal logic of the oscillators 14 and 18.

In practice, the value L14 is negligible with respect to the value K14\*Z12, e.g., less than one thousandth of the value K14\*Z12. Similarly, the value L18 is in practice negligible with respect to the value K18\*Z20, e.g., less than one thousandth of the value K18\*Z20. Thereby, the value DIGOUT1 is obtained by the following equation:

$$DIGOUT1 = PV * (K18 * Z20)/(K14 * Z12).$$

Taking the example of a supply voltage of value VDD, the value DIGOUT1, supplied by the counter 16 at the end of the first phase, is given by to the following equation:

$$DIGOUT1 = PV * (K18 * Z20)/(K14 * Z12).$$

With a supply voltage of value VDD', the value DIGOUT1', supplied by the counter 16 at the end of the first phase, is given by the following equation:

$$DIGOUT1' = PV * (K18' * Z20)/(K14' * Z12).$$

Thereby, the values DIGOUT1 and DIGOUT1' obey the following equation:

$$DIGOUT1' = DIGOUT1 * (K18'/K18)/(K14'/K14).$$

Since the oscillators 14 and 18 are identical, within manufacturing variations, the values K14 and K18 have close values. The values K14 and K18 are assumed to obey the following equation, corresponding to the first order expansion:

$$K18 = K14 * (1 + eK),$$

the eK value being, in practice, generally less than or equal to 5%.

The values K14, K14', K18 and K18' thus obey the following equations, corresponding to the first order expansion:

$$K14' = K14 * (1 + e14); \text{ and}$$
$$K18' = K18 * (1 + e18),$$

the values e14 and e18 being, in practice, generally less than or equal to 5%.

Thereby, the values DIGOUT1 and DIGOUT1' obey the following equation:

$$DIGOUT1' = DIGOUT1 * (1 + e18)/(1 + e14).$$

According to a first order estimation, if the values a and b are less than 5%, the following equations are true:

$$1/(1 + b) \sim 1 - b; \text{ and}$$
$$(1 + a)/(1 + b) \sim 1 + a - b.$$

Thereby, the values DIGOUT1 and DIGOUT1' obey the following equation:

$$DIGOUT1' \sim DIGOUT1*(1+e18-e14).$$

It can thus be seen that, at the end of the first phase, the value obtained by the counter 16 remains dependent on a variation in the supply voltage, the values DIGOUT1 and DIGOUT1' being different.

FIG. 2B schematically illustrates another step of an embodiment of the analog-digital converter shown in FIG. 1. More precisely, FIG. 2B illustrates a second step during which the converter is in the second operating mode.

In the second operating mode, the enabling signal RUNA received by the oscillator 14 corresponds to the signal RUN1 and the enabling signal RUNB received by the oscillator 18 corresponds to the signal RUN2.

According to one embodiment, the counter 16 is not reinitialized between the first and second phases or steps, i.e., between the step illustrated by FIG. 2A and the step illustrated by FIG. 2B. The counter 22 is reset and the value PV is not modified.

Like in the first operating mode, when the second step is started, the signal RUNA takes the value RUN1 equal to 1, indicating the enabling of the converter. Taking the example of a reset counter 22 (yet the following discussion can be transposed to the case where the value PV is doubled), the signal CO is in the state 0 and the signal RUN2, applied to the input RUNB of the oscillator 18, is equal to 1.

The oscillators 14 and 18 generate voltages having the frequencies f14 and f18, respectively. The values DIGOUT and PVOUT increase, the counters 22 and 16 counting the oscillations of the voltages generated by the oscillators 14 and 18. When the value PVOUT, this time linked to the oscillator 14, reaches the reference value PV, the signal RUN2 takes the value 0 and stops the oscillator 18. The output of the counter 16, and thus the value DIGOUT, becomes stable again.

The oscillation time D2, i.e., the time between the enabling and the stopping of the oscillator 18 obeys, assuming the resetting of the counter 22 between the two phases, the following equation:

$$D2 = DIGOUT2*t18(D12)$$

$$= PV*t14(D20),$$

wherein DIGOUT2 is the value by which the value DIGOUT has increased during the time D2, i.e., the difference between the value DIGOUT1 at the beginning of the first step and the value DIGOUT at the end of the second step.

In other words, the value DIGOUT2 is obtained by the following equation:

$$DIGOUT2 = PV*t14(D20)/t18(D12)$$

$$= PV*f18(D12)/f14(D20),$$

wherein f18 (D12) corresponds to the frequency of the oscillator 18 associated with the element 12 and f14 (D20) corresponds to the frequency of the oscillator 14 associated with the element 20.

The oscillation time D2, i.e., the time between the enabling and the stop of oscillator 18, obeys the following equation:

$$D2 = DIGOUT2*t18(D12)$$

$$= PV*t14(D20),$$

wherein DIGOUT2 is the value by which the value DIGOUT has increased during D2, PV is the value by which the PVOUT value has increased during the time D2 and is equal to the value by which the value PVOUT has increased during the time D1, i.e., the reference value, t18 (D12) corresponds to the period of the oscillator 18 associated with the element 12 and t14 (D20) corresponds to the period of the oscillator 14 associated with the element 20. In other words, the value DIGOUT2 is obtained by the following equation:

$$DIGOUT2 = PV*t14(D20)/t18(D12)$$

$$= PV*f18(D12)/f14(D20),$$

wherein f18 (D12) corresponds to the frequency of the oscillator 18 associated with the element 12 and f14 (D20) corresponds to the frequency of the oscillator 14 associated with the element 20. The reference value PV of the second step is equal to twice the reference value of the first step.

The periods of the oscillators 14 and 18 are obtained, in a similar manner to the periods of the first operating mode, by the following equations:

$$t18(D12) = K18*Z12 + L18; \text{ and}$$

$$t14(D20) = K14*Z20 + L14.$$

By neglecting, like for the first step, the values L14 and L18, the value DIGOUT2 is given by the following equation:

$$DIGOUT2 = PV*(K14*Z20)/(K18*Z12)$$

$$= PV*(K14*Z20)/(K18*Z12).$$

Like in the first step, in the case where the supply voltage is a voltage VDD, the value DIGOUT2 corresponds to the following equation:

$$DIGOUT2 = PV*(K14*Z20)/(K18*Z12).$$

In the case where the supply voltage is another voltage VDD', the value DIGOUT2' corresponds to the following equation:

$$DIGOUT2' = PV*(K14'*Z20)/(K18'*Z12).$$

Thereby, the values DIGOUT2 and DIGOUT2' obey the following equation:

$$DIGOUT2' = DIGOUT2 * (K14'/K14)/(K18'/K18).$$

The first order developments performed for the first step are performed similarly for the second step. Thereby, the following equations are considered true:

$$K18 = K14 * (1 + eK);$$
$$K14' = K14 * (1 + e14);\ \text{and}$$
$$K18' = K18 * (1 + e18).$$

Thereby, the values DIGOUT2 and DIGOUT2' obey the following equation:

$$DIGOUT2' = DIGOUT2 * (1 + e14)/(1 + e18).$$

Thereby, the values DIGOUT2 and DIGOUT2' obey the following equation:

$$DIGOUT2' = DIGOUT2 * (1 + e14 - e18).$$

The value DIGOUT3, corresponding to the value DIGOUT at the end of the first and second steps, is equal to the sum of the value DIGOUT1 and the value DIGOUT2. Thereby, the value DIGOUT3 obeys the following equation:

$$
\begin{aligned}
DIGOUT3 &= PV * (K18 * Z20)/(K14 * Z12) + \\
&\quad PV * (K14 * Z20)/(K18 * Z12) \\
&= PV * (Z20/Z12) * (K18/K14 + K14/K18) \\
&= PV * (Z20/Z12) * (1 + eK + 1 - eK) \\
&= 2 * PV * (Z20/Z12).
\end{aligned}
$$

Similarly, for a supply voltage VDD', the value DIGOUT3' is equal to the sum of the values DIGOUT1' and DIGOUT2'. Thereby, the value DIGOUT3' obeys the following equations:

$$
\begin{aligned}
DIGOUT3' &= PV * (Z20/Z12) * (K18'/K14' + K14'/K18') \\
&= PV(Z20/Z12) * [(K18/K14) * (1 + e18)/(1 + e14) + (K14/K18) * (1 + e14)/(1 + e18)] \\
&= PV * (Z20/Z12) * [(1 + eK) * (1 + e18)/(1 + e14) + (1 - eK) * (1 + e14)/(1 + e18)] \\
&= PV * (Z20/Z12) * [(1 + eK) * (1 + e18 - e14) + (1 - eK) * (1 + e14 - e18)] \\
&\sim PV * (Z20/Z12) * [(1 + e18 - e14 + eK) + (1 + e14 - e18 + eK)]
\end{aligned}
$$

Thereby, the value DIGOUT3' obeys the following equation: DIGOUT3'~DIGOUT1'+DIGOUT2'~2*PV*(Z20/Z12)

It appears that, in first order, DIGOUT1'+DIGOUT2' is equal to DIGOUT1+DIGOUT2. Thereby, the value obtained at the end of the two steps is, in first order, independent of the supply voltage.

The result of the counting at the end of the two steps is twice the result of one step. In order to obtain the value representative of the physical quantity measured, a reference value divided by two can be used at the comparator for the two steps, in order to compensate for the difference 1.

Figure 3:
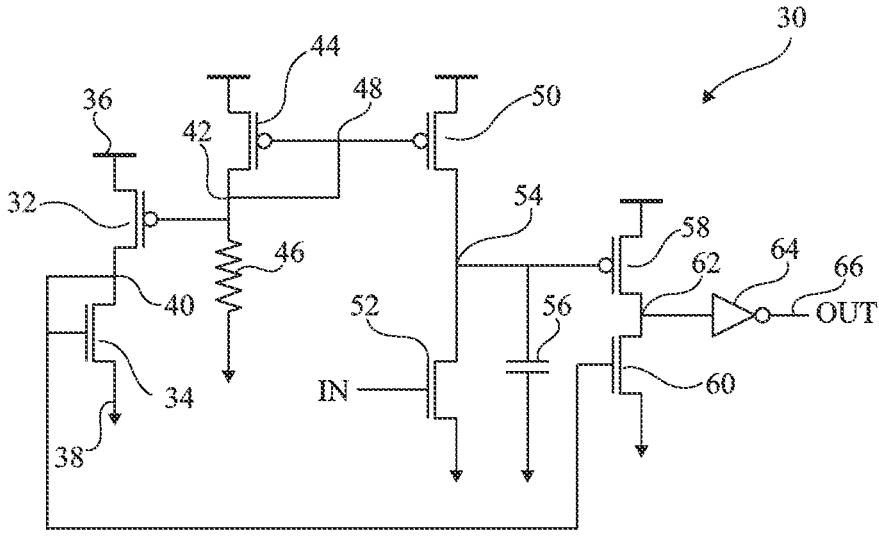
FIG. 3 illustrates an example of embodiment of a part of the embodiment shown in FIG. 1.

FIG. 3 shows an example of implementation of a part of the embodiment shown in FIG. 1. More precisely, FIG. 3 shows an example of implementation of a delay circuit 30 that is weakly dependent on the supply voltage. The circuit 30 is comprised of each oscillator 14 and 18. The circuit 30 determines the frequency of the oscillator and ensures that the first order estimations of the coefficients K14 and K18 can be made.

The circuit 30 comprises transistors 32 and 34 connected in series between a node 36 for applying the supply voltage VDD and a node 38 for applying a reference voltage, e.g., the ground. The transistors 32 and 34 are e.g., Metal Oxide Semiconductor Field-Effect Transistors, or MOSFETs. The transistor 32 is e.g., a P-channel transistor and the transistor 34 is e.g., an N-channel transistor.

One terminal of the transistor 32, e.g., the source, is linked, preferentially connected, to the node 36 and another terminal of the transistor 32, e.g., the drain, is linked, preferentially connected, to a node 40. One terminal of the transistor 34, e.g., the drain, is linked, preferentially connected, to the node 40 and another terminal of the transistor 34, e.g., the source, is linked, preferentially connected, to the node 38. The transistor 34 comprises a control terminal linked, preferentially connected, to the node 40. The transistor 32 comprises a control terminal linked to a node 42. A current Irefn flows through the transistor 34.

The circuit 30 comprises a transistor 44 and a resistor 46 connected in series between the node 36 and the node 38. The transistor 44 is e.g., a MOSFET, e.g., a P-channel transistor. One terminal of the transistor 44, e.g., the source, is linked, preferentially connected, to the node 36 and the other terminal of the transistor 44, e.g., the drain, is linked, preferentially connected, to the node 42. One terminal of the resistor 46 is linked, preferentially connected, to the node 42 and another terminal of the resistor 46 is linked, preferentially connected, to the node 38. The transistor 44 comprises a control terminal linked, preferentially connected, to a node 48. The node 48 is further linked, preferentially connected, to the node 42.

The circuit 30 comprises transistors 50 and 52 connected in series between the node 36 of application of the supply voltage VDD and the node 38 of application of a reference voltage, e.g., the ground. The transistors 50 and 52 are e.g., Metal Oxide Semiconductor Field-Effect Transistors, or MOSFETs. The transistor 50 is e.g., a P-channel transistor and the transistor 52 is e.g., an N-channel transistor. A current equal to 1/n times the current flowing through transistor 44, flows through the transistor 50. Indeed, the assembly 44 and 50 is a current mirror. The transistor 52 operates in switching mode, i.e., same discharges the capacitor 56 if the voltage IN, i.e., the voltage applied to the gate of the transistor 52, is equal to the supply voltage, and allows the capacitor to be charged if the voltage IN is equal to the ground potential. The transistor 50 is configured so that the size of the transistor 44 is n times greater than the size of the transistor 50. For example, the transistors 44 and 50 are each formed by a plurality of elementary transistors identical to each other and connected in parallel. The transistor 44 comprises n times more elementary transistors than transistor 50.

One terminal of the transistor 50, e.g., the source, is linked, preferentially connected, to the node 36 and another terminal of the transistor 50, e.g., the drain, is linked, preferentially connected, to a node 54. One terminal of the transistor 52, e.g., the drain, is linked, preferentially connected, to the node 54 and another terminal of the transistor 52, e.g., the source, is linked, preferentially connected, to the node 38. The transistor 50 comprises a control terminal linked, preferentially connected, to the node 48. The transistor 52 comprises a control terminal linked, preferentially connected, to a node for applying an input voltage IN.

The circuit 30 further comprises a capacitor 56 linked between the node 54 and the node 38. In other words, one terminal of the capacitor is linked, preferentially connected, to the node 54 and another terminal of the capacitor is linked, preferentially connected, to the node 38.

The circuit 30 comprises transistors 58 and 60 connected in series between the node 36 of application of the supply voltage VDD and the node 38 of application of a reference voltage, e.g., the ground. The transistors 58 and 60 are e.g., Metal Oxide Semiconductor Field-Effect Transistors, or MOSFETs. The transistor 58 is e.g., a P-channel transistor and the transistor 60 is e.g., an N-channel transistor.

One terminal of the transistor 58, e.g., the source, is linked, preferentially connected, to the node 36 and another terminal of the transistor 58, e.g., the drain, is linked, preferentially connected, to a node 62. One terminal of the transistor 60, e.g., the drain, is linked, preferentially connected, to the node 62 and another terminal of the transistor 60, e.g., the source, is linked, preferentially connected, to the node 38. The transistor 58 comprises a control terminal linked, preferentially connected, to the node 54. The transistor 60 comprises a control terminal linked, preferentially connected, to the node 40. Thereby, the transistor 60 is mounted as a source of current, reproducing the current flowing through the transistor 34.

The circuit 30 comprises e.g., an inverter 64 linked between the node 62 and an output node 66, on which an output voltage OUT is generated. The inverter 64 comprises an input terminal linked, preferentially connected, to the node 62 and an output terminal linked, preferentially connected, to the node 66.

The circuit 30 is configured for generating the output signal OUT in such a way that, for each falling edge of the signal IN, the signal OUT comprises a rising edge, delayed by a time t. The time t is configured for being equal to the product of the number n, the resistance value 46 and the capacitance value of the capacitor 56. Moreover, for each rising edge of the signal IN, the circuit 30 is configured so that the signal OUT comprises a falling edge without delay.

The delay generated by the circuit 30 is, theoretically, constant and independent of the value of the supply voltage. However, the delay generated depends on the switching point of the inverter 64. The switching point is dependent on the supply voltage.

Figure 4:
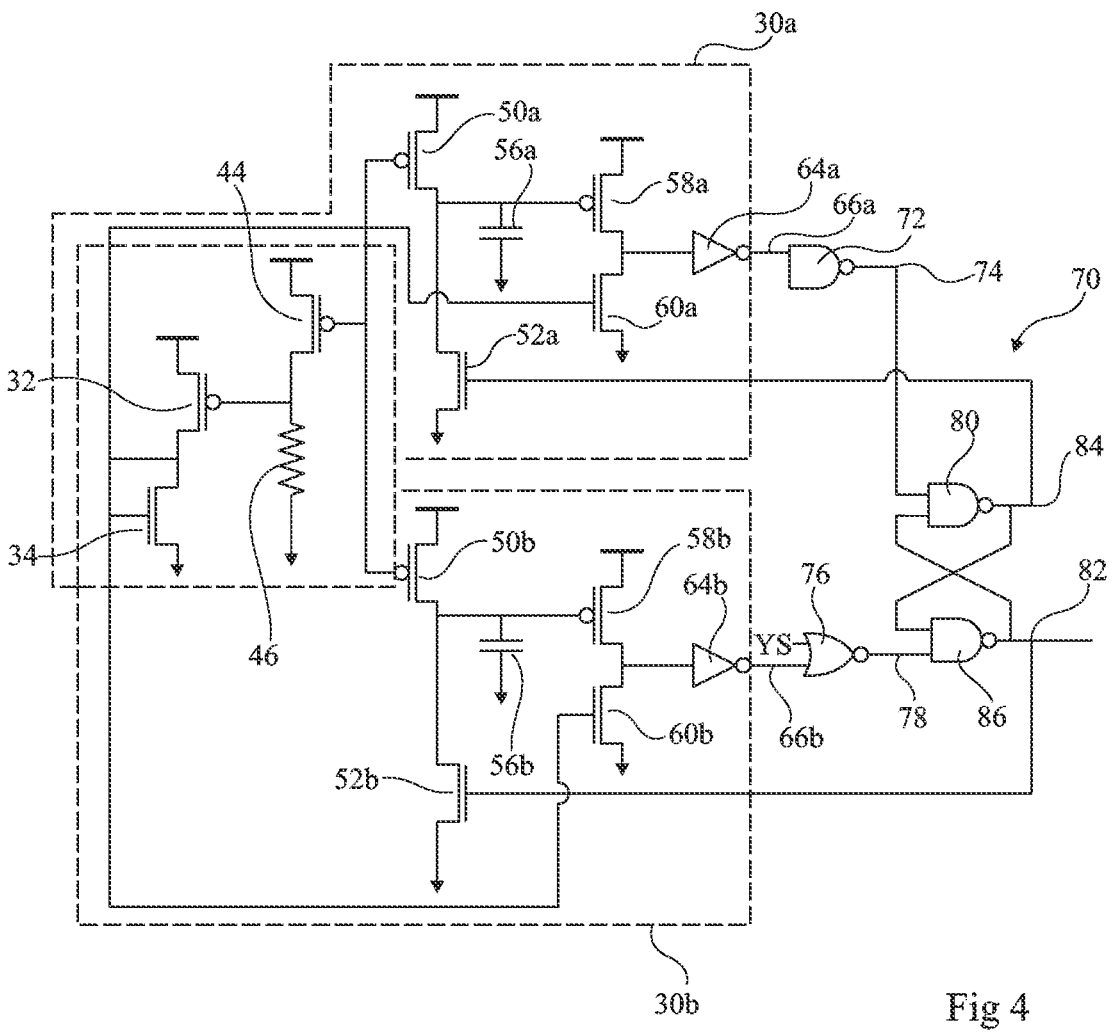
FIG. 4 illustrates an example of embodiment of another part of the embodiment shown in FIG. 1.

FIG. 4 shows an example of implementation of another part of the embodiment shown in FIG. 1. More precisely, FIG. 4 schematically illustrates an oscillator 70. The oscillator 70 corresponds e.g., to the oscillator 14 or 18.

The oscillator 70 comprises two circuits 30a and 30b each corresponding to a circuit such as the circuit 30 shown in FIG. 3. The transistors 32, 34, 44 and the resistor 46 are e.g., common to the circuits 30a and 30b. The circuit 30a comprises transistors 50a, 52a, 58a, 60a, a capacitor 56a and an inverter 64a linked to each other and to the transistors 32, 34, 44 and to the resistor 46 like the transistors 50, 52, 58, 60, the capacitor 56 and the inverter 64, respectively, shown in FIG. 3. Similarly, the circuit 30 comprises transistors 50b, 52b, 58b, 60b, a capacitor 56b and an inverter 64b linked to each other and to the transistors 32, 34, 44 and to the resistor 46 like the transistors 50, 52, 58, 60, the capacitor 56 and the inverter 64, respectively, shown in FIG. 3. In addition, the circuits 30a and 30b comprise output nodes 66a and 66b, respectively, corresponding to the node 66 shown in FIG. 3.

The oscillator 70 further comprises a NAND logic gate 72. The gate 72 comprises a first input linked, preferentially connected, to the node 66a and a second input linked, preferentially connected, to a node for applying a signal S. The gate 72 further comprises an output linked, preferentially connected, to a node 74.

The oscillator 70 further comprises a NOR logic gate 76. The gate 76 comprises a first input linked, preferentially connected, to the node 66b and a second input linked, preferentially connected, to a node of application of a signal/S, corresponds e.g., to the signal complementary to the signal S. The gate 76 further comprises an output linked, preferentially connected, to a node 78.

The oscillator 70 further comprises a NAND logic gate 80. The gate 80 comprises a first input linked, preferentially connected, to the node 74 and a second input linked, preferentially connected, to a node 82 corresponding to the output of the oscillator 70. The gate 80 further comprises an output linked, preferentially connected, to a node 84. The node 82 is linked, preferentially connected, to the control terminal of the transistor 52b. Similarly, the node 84 is linked, preferentially connected, to the control terminal of the transistor 52a.

The oscillator 70 further comprises a NAND logic gate 86. The gate 86 comprises a first input linked, preferentially connected, to the node 78 and a second input linked, preferentially connected, to the node 84. The gate 86 further comprises an output linked, preferentially connected, to a node 82.

In the embodiments shown in FIGS. 1, 2A and 2B, the resistor 46 is replaced by the corresponding device 12 or 20.

An advantage of the described embodiments is that the analog-digital conversion is less prone to errors due to the variations of supply voltage, to aging, and to variations in the manufacturing process, particularly if the oscillators are further configured, e.g., by known techniques, for reducing the dependence of the frequencies f14 and f18 on the variations of the supply voltage, on aging, and on the variations in the manufacturing process, and to ensure that the frequencies of the oscillators 14 and 18 are close.

Various embodiments and variants have been described. Those skilled in the art will understand that certain features of these embodiments can be combined and other variants will readily occur to those skilled in the art.

Finally, the practical implementation of the embodiments and variants described herein is within the capabilities of those skilled in the art based on the functional description provided hereinabove.

US 12,627,311 B2

15

What is claimed is:

1. A method for controlling an analog-digital converter comprising first and second oscillators and first and second elements, the method comprising:

generating, in a first step by the first and second oscillators, frequencies depending on an electrical characteristic of the first element and of the second element, respectively; and generating, in a second step by the first and second oscillators, frequencies depending on the electrical characteristic of the second element and of the first element, respectively;

the electrical characteristic of the first element being sensitive to variations of a physical quantity, and the electrical characteristic of the second element being insensitive or inversely sensitive to the variations of the physical quantity.

2. The method according to claim 1, wherein the first and second oscillators are identical.

3. The method according to claim 1, wherein the electrical characteristic of the second element is insensitive to the variations of the physical quantity.

4. The method according to claim 1, wherein the first element is a sensor.

5. The method according to claim 1, wherein the analog-digital converter comprises first and second counters, and the method further comprises:

during the first step, counting, by the first counter, first oscillations of the first oscillator, and counting, by the second counter, first oscillations of the second oscillator; and during the second step, counting, by the first counter, second oscillations of the second oscillator, and counting, by the second counter, second oscillations of the first oscillator.

6. The method according to claim 5, further comprising:

reaching, by the second counter, a reference value; and triggering, by the second counter in response to reaching the reference value, a stopping of the oscillator associated with the first counter.

7. The method according to claim 5, further comprising providing, by the first and second counters, counter values representative of first values of the respective electrical characteristics of the first and second elements.

8. The method according to claim 7, further comprising:

providing, by the first counter, a counter value representative of a current first value of the physical quantity.

9. The method according to claim 5, further comprising generating, by a circuit of the analog-digital converter, a control signal of the oscillator associated with the first element depending on a state of an enabling signal of the oscillator associated with the second element and on a value of the second counter.

10. An analog-digital converter comprising:

first and second elements; and first and second oscillators, wherein the first and second oscillators are configured to:

generate, during a first step, frequencies depending on an electrical characteristic of the first element and of the second element, respectively; and generate, during a second step, frequencies depending on the electrical characteristic of the second element and of the first element, respectively;

wherein the electrical characteristic of the first element is sensitive to variations of a physical quantity, and the electrical characteristic of the second element is insensitive or inversely sensitive to the variations of the physical quantity.

11. The analog-digital converter according to claim 10, wherein the first and second oscillators are identical.

12. The analog-digital converter according to claim 10, wherein the electrical characteristic of the second element is insensitive to the variations of the physical quantity.

13. The analog-digital converter according to claim 10, wherein the first element is a sensor.

14. The analog-digital converter according to claim 10, wherein the analog-digital converter further comprises:

a first counter configured to:

during the first step, count first oscillations of the first oscillator; and during the second step, count first oscillations of the second oscillator; and a second counter configured to:

during the first step, count second oscillations of the second oscillator; and during the second step, count second oscillations of the first oscillator.

15. The analog-digital converter according to claim 14, wherein the second counter is configured to:

reach a reference value; and trigger, in response to reaching the reference value, a stopping of the oscillator associated with the first counter.

16. The analog-digital converter according to claim 14, wherein the first and second counters are configured to provide counter values representative of first values of the respective electrical characteristics of the first and second elements.

17. The analog-digital converter according to claim 16, wherein:

the first counter is configured to provide a counter value representative of a current first value of the physical quantity.

18. The analog-digital converter according to claim 14, wherein the analog-digital converter further comprises:

a circuit configured to generate a control signal of the oscillator associated with the first element depending on a state of an enabling signal of the oscillator associated with the second element and on a value of the second counter.

19. An analog-digital converter comprising:

first and second sensors;

first and second oscillators, wherein the first and second oscillators are configured to:

generate, during a first step, frequencies depending on an electrical characteristic of the first sensor and of the second sensor, respectively; and generate, during a second step, frequencies depending on the electrical characteristic of the second sensor and of the first sensor, respectively; and a first counter configured to:

during the first step, count first oscillations of the first oscillator; and during the second step, count first oscillations of the second oscillator; and a second counter configured to:

during the first step, count second oscillations of the second oscillator; and during the second step, count second oscillations of the first oscillator;

wherein the electrical characteristic of the first sensor is sensitive to variations of a physical quantity, and the electrical characteristic of the second sensor is insensitive or inversely sensitive to the variations of the physical quantity.

20. The analog-digital converter according to claim 19, wherein:

the first and second oscillators are identical; and the electrical characteristic of the second sensor is insensitive to the variations of the physical quantity.

* * * * *